United States Patent
Gall et al.

(10) Patent No.: US 7,329,330 B2
(45) Date of Patent: Feb. 12, 2008

(54) METHOD AND DEVICE FOR THE DISTILLATIVE PROCESSING OF 1,6-HEXANEDIOL, 1,5-PENTANEDIOL AND CAPROLACTONE

(75) Inventors: Martin Gall, Mutterstadt (DE); Gerd Kaibel, Lampertheim (DE); Thomas Krug, Worms (DE); Harald Rust, Neustadt (DE); Frank Stein, Bad Dürkheim (DE)

(73) Assignee: Basf Aktiengesellschaft, Ludwigshafen (DE)

( * ) Notice: Subject to any disclaimer, the term of this patent is extended or adjusted under 35 U.S.C. 154(b) by 328 days.

(21) Appl. No.: 10/451,738

(22) PCT Filed: Jan. 8, 2002

(86) PCT No.: PCT/EP02/00105

§ 371 (c)(1),
(2), (4) Date: Jun. 25, 2003

(87) PCT Pub. No.: WO02/055460

PCT Pub. Date: Jul. 18, 2002

(65) Prior Publication Data

US 2004/0040829 A1    Mar. 4, 2004

(30) Foreign Application Priority Data

Jan. 9, 2001    (DE) .................. 101 00 552

(51) Int. Cl.
*B01D 3/14* (2006.01)
*B01D 3/42* (2006.01)
*C07C 29/80* (2006.01)

(52) U.S. Cl. ............ 203/1; 203/2; 203/3; 203/78; 203/80; 203/99; 203/DIG. 19; 202/158; 196/111; 568/913

(58) Field of Classification Search .............. 203/1–3, 203/78, 80, 99, DIG. 19; 202/153–155, 202/158, 172; 196/111; 568/864, 913
See application file for complete search history.

(56) References Cited

U.S. PATENT DOCUMENTS 4,230,533 A * 10/1980 Giroux .................. 203/1

(Continued)

FOREIGN PATENT DOCUMENTS

DE    19607954    9/1997

(Continued)

*Primary Examiner*—Virginia Manoharan
(74) *Attorney, Agent, or Firm*—Novak Druce & Quigg, LLP

(57) ABSTRACT

A process for working up by distillation the crude products obtained in the process according to DE-A 196 07 954 and containing 1,6-hexanediol (HDO), 1,5-pentanediol (PDO) or caprolactone (CLO) in order to obtain the corresponding pure products, the working-up by distillation being carried out in each case in a dividing wall column (TK) in which a dividing wall (T) is arranged in the longitudinal direction of the column with formation of an upper common column region (1), a lower common column region (6), a feed section (2, 4) having a rectification section (2) and stripping section (4), and a take-off section (3, 5) having a stripping section (3) and rectification section (5), with feeding of the respective crude product HDO, PLO or CLO in the middle region of the feed section (2, 4) and removal of the high boiler fraction (C) from the bottom of the column, of the low boiler fraction (A) via the top of the column and of the medium boiler fraction (B) from the middle region of the take-off section (3, 5), or in thermally coupled columns.

37 Claims, 2 Drawing Sheets

U.S. PATENT DOCUMENTS

| | | | |
|---|---|---|---|
| 4,994,152 A | 2/1991 | Kaibel et al. | 203/75 |
| 5,914,012 A | 6/1999 | Kaibel et al. | 202/158 |
| 5,981,769 A | 11/1999 | Baur et al. | 549/266 |
| 6,288,286 B1 * | 9/2001 | Stein et al. | 568/864 |
| 6,387,222 B1 * | 5/2002 | Tragut et al. | 203/2 |
| 6,846,389 B2 * | 1/2005 | Kaibel et al. | 203/1 |

FOREIGN PATENT DOCUMENTS

| | | | |
|---|---|---|---|
| EP | 122367 | 1/1984 | |
| EP | 0 122 367 | * 10/1984 | |
| EP | 380001 | 8/1990 | |
| EP | 640367 | 3/1995 | |
| EP | 0 780 147 | * 12/1996 | |
| EP | 804951 | 11/1997 | |
| WO | 01/85708 | * 3/2001 | |

\* cited by examiner

METHOD AND DEVICE FOR THE DISTILLATIVE PROCESSING OF 1,6-HEXANEDIOL, 1,5-PENTANEDIOL AND CAPROLACTONE

FIELD OF THE INVENTION

The present invention relates to a process for working up by distillation the crude products 1,6-hexanediol, 1,5-pentanediol and caprolactone obtained in the process according to DE-A 196 07 954 and referred to below as HDO, PDO and CLO, respectively, for short, and to an apparatus for carrying out the process.

BACKGROUND OF THE INVENTION

HDO, PDO and CLO are important monomer building blocks, in particular for the preparation of polyesters and polyurethanes. Said substances can be obtained, with the high purity required for the intended use mentioned, preferably of at least 99%, in particular virtually free of 1,4-cyclohexanediol, by a known process described in DE-A 196 07 954, from a complex carboxylic acid mixture which is obtained as a byproduct of the oxidation of cyclohexane to cyclohexanone/cyclohexanol. In the process described in DE 196 07 954, a starting mixture itself generally referred to as dicarboxylic acid solution (DCS), is a complex mixture of a large number of substances. A hydrogenation discharge is obtained therefrom in 5 stages by a multistage process, from which discharge a stream containing predominantly 1,6-hexanediol in addition to 1,5-pentanediol is obtained by distillation in stage 6. A 1,5-pentanediol-containing top stream, from which 1,5-pentanediol is obtained as a pure product by distillation, and a side stream containing 1,6-hexanediol as pure product is taken off therefrom in stage 7 by separation by distillation.

Cyclization of a stream containing predominantly 6-hydroxycaproic esters in stage 13 gives caprolactone, which is worked up in stage 14 by distillation. Owing to the complex mixtures of substances, it was surprising that, in spite of the unfavorable boiling point conditions and risk of azeotrope formation, the target products HDO, PDO and CLO could be obtained by distillation in high purity, in particular HDO with a very small residual 1,4-cyclohexanediol content.

Dividing wall columns, i.e. distillation columns having vertical dividing walls which prevent cross-mixing of liquid streams and vapor streams in certain regions, are known for the separation of multicomponent mixtures by distillation. The dividing wall, which can preferably consist of a metal sheet, divides the middle region of the column in the longitudinal direction into a feed section and a take-off section.

A similar result can be achieved with thermally coupled columns, i.e. arrangements of at least two columns where each of the columns has at least two links with each other column at spatially separate points.

SUMMARY OF THE INVENTION

It is an object of the present invention to provide an improved, in particular more economical process for obtaining the pure products HDO, PLO and CLO from the corresponding crude products obtained in the process according to DE-A 196 07 954.

We have found that this object is achieved by a process for separating by distillation the crude products obtained in the process according to DE-A 196 07 954 and containing 1,6-hexanediol (HDO), 1,5-pentanediol (PDO) and caprolactone (CLO) to obtain the corresponding pure products.

In the invention, the working-up by distillation is carried out in each case in a dividing wall column (TK) in which a dividing wall (T) is arranged in the longitudinal direction of the column with formation of an upper common column region, a lower common column region, a feed section having rectification section and stripping section, and a take-off section having a stripping section and rectification section, with feeding of the respective crude product HDO, PLO or CLO in the region of the feed section and removal of the high boiler fraction (C) from the bottom of the column, of the low boiler fraction (A) via the top of the column and of the medium boiler fraction (B) from the region of the take-off section, or in thermally coupled columns.

It has surprisingly been found that the demanding object of isolating the pure products HDO, PDO and CLO by distillation from the corresponding crude products obtained in the process according to DE-A 196 07 954 can also be successfully achieved in the dividing wall columns or thermally coupled columns, which are known to be more difficult to control.

Said crude products are complex mixtures which typically have compositions as stated below; as usual, low boilers are defined here as substances whose boiling point is below that of the respective main product and high boilers are defined as substances whose boiling point is above that of the respective main product.

Crude HDO contains, in addition to the main product HDO, as a rule from about 15 to 23% by weight of low boilers, including in particular PDO, 1,2-cyclohexanediol, hexanol, butanediol and caprolactone, as well as from about 2 to 4% of high boilers, in particular di-HDO ethers and hydroxycaproic acid HDO ethers.

Crude PDO contains, in addition to the main product PDO, as a rule from about 15 to 30% by weight of low boilers (1,2-cyclohexanediol, hexanol, butanediol), as well as from about 20 to 50% by weight of high boilers, in particular HDO.

Crude CLO contains, in addition to the main product CLO, as a rule from 1.5 to 3.0% by weight of low boilers, mostly methanol, valerolactone, unsaturated valerolactone, formic acid PDO esters and from about 0.1 to 1% by weight of high boilers, in particular dimeric CLO, formic acid/hydroxycaproic acid methyl esters and hydroxycaproic acid methyl ester.

The term pure product with respect to HDO, PDO and CLO is understood here in each case as meaning a mixture which is defined as follows:

Pure HDO contains at least 98, in particular at least 99, particularly preferably at least 99.7, % by weight of 1,6-hexanediol, the remainder being impurities, in particular heptanediol, 1,4-cyclohexanediol, 1,2-cyclohexanediol and PDO.

Pure PDO contains at least 93, in particular at least 95, particularly preferably at least 97, % by weight of 1,5-pentanediol, the remainder being impurities, mainly HDO, 1,4-cyclohexanediol, CLO, 1,2-cyclohexanediol and 1,4-butanediol.

Pure CLO contains at least 99, in particular at least 99.5, particularly preferably at least 99.9, % by weight of caprolactone, the remainder being impurities, mainly hydroxycaproic acid methyl ester, formic acid/hydroxycaproic acid methyl esters, 1,2-cyclohexanediol, formic acid, PDO ester and valerolactone.

Dividing wall columns typically have a dividing wall which divides the interior of the column into the following regions: an upper common column region, a lower common column region and a feed section and a take-off section, in each case having a rectification section and stripping section. The mixture to be separated is introduced in the region of the feed section, a high boiler fraction is removed from the bottom of the column, a low boiler fraction is removed via the top of the column and a medium boiler fraction is removed from the region of the take-off section.

In the separation of multicomponent mixtures into a low boiler, a medium boiler and a high boiler fraction, there are usually specifications regarding the maximum permissible proportion of low boilers and high boilers in the medium boiler fraction. Here, components critical for the separation problem, i.e. key components, are specified. These may comprise an individual key component or the sum of a plurality of key components. In the present process, key components of the HDO purification by distillation are BDO (low boiler) and heptanediol (high boiler). Key components of the PDO purification by distillation are 1,2-cyclohexanediol (low boiler) and HDO (high boiler). Key components of the CLO purification by distillation are valerolactone (low boiler) and hydroxycaproic acid methyl ester (high boiler).

In a preferred process variant, compliance with the specification regarding the key components is ensured by regulating the distribution ratio of the liquid at the upper end of the dividing wall and the heating power of the evaporators in a specific manner. The distribution ratio of the liquid at the upper end of the dividing wall is set in a manner such that the proportion of high-boiling key components in the liquid reflux via the stripping section of the take-off section is from 10 to 80%, preferably from 30 to 50%, of the limit permitted in the medium boiler fraction, and the heating power in the bottom evaporator of the dividing wall column is set in a manner such that the concentration of the low-boiling key components in the liquid at the lower end of the dividing wall is from 10 to 80%, preferably from 30 to 50%, of the limit permitted in the medium boiler stream. Accordingly, in the case of this regulation, the liquid distribution at the upper end of the dividing wall is set so that more liquid is passed to the feed section at higher contents of high-boiling key components and less liquid is passed to said section at lower contents thereof. Analogously, the regulation of the heating power is carried out so that the heating power is increased at a higher content of low-boiling key components and the heating power is reduced at a lower content thereof.

It was found that a further improvement of the process can be achieved by ensuring a substantially uniform liquid feed by corresponding regulation methods. Disturbances of the feed rate or of the feed concentration are compensated. For this purpose, it is ensured according to the invention that the flow rate of the liquid which is fed to the lower part of the feed section does not fall below 30% of its normal value.

Preferably, the distribution of the liquid flowing out of the stripping section of the take-off section of the dividing wall column between the medium boiler fraction taken off and the rectification section of the take-off section of the dividing wall column is also regulated in a manner such that the amount of liquid added to the rectification section does not fall below 30% of its normal value.

Preferably, the HDO purification columns and the PDO purification columns are connected so that the HDO fractions remaining in the top stream of the HDO column are recovered via the bottom of the PDO purification column and are recycled to the HDO purification column.

The medium boiler fraction is preferably taken off in liquid form; this process variant is thermally advantageous and simpler to realize in terms of apparatus.

In a preferred process variant, the vapor stream at the lower end of the dividing wall can be set in a manner such that the ratio of the vapor stream in the feed section to the vapor stream in the take-off section is from 0.8 to 1.2, preferably from 0.9 to 1.1, preferably by the choice and/or dimensioning of internals having a separating effect and/or by the installation of means which generate a pressure drop.

In a further preferred process variant, the reflux from the upper common column section can be regulated so that the ratio of the reflux stream in the feed section to the reflux in the take-off section is from 0.1 to 1, preferably from 0.5 to 0.8.

More preferably, the top stream can be taken off in a temperature-controlled manner, the measuring point for the control temperature in the upper common region of the column being arranged at a point which is from 3 to 8, preferably from 4 to 6, theoretical plates below the upper end of the column.

According to a further preferred process variant, the high boiler stream can be taken off in a temperature-controlled manner, the measuring point for the control temperature in the lower common column region being arranged from 3 to 8, preferably from 4 to 6, theoretical plates above the lower end of the column.

According to a further process variant, the medium boiler stream is taken off under level control, the liquid level in the evaporator or in the bottom of the column being used as a control variable.

The present invention also relates to a dividing wall column for carrying out the novel process. Dividing wall columns having from 30 to 100, preferably from 50 to 90, theoretical plates are particularly suitable for this purpose.

The distribution of the number of theoretical plates over the individual regions of the dividing wall column is preferably effected in a manner such that each of the 6 column regions of the dividing wall column has from 5 to 50%, preferably from 15 to 30%, of the total number of theoretical plates of the dividing wall column.

In a preferred embodiment of the dividing wall column, the feed point of the stream to be separated and the take-off point of the medium boiler stream may be arranged at different heights in the column, preferably from 1 to 20, in particular from 10 to 15, theoretical plates apart.

Regarding the internals which have a separating effect and may be used in the dividing wall column, there are in principle no restrictions: both dumped packings and stacked packings or trays are suitable for this purpose. For cost reasons, trays, preferably valve trays or sieve trays, are generally used in columns having a diameter of more than 1.2 m.

In the case of the columns having stacked packings, stacked sheet metal packings having a specific surface area of from 100 to 500, preferably from about 250 to 300, $m^2/m^3$ are particularly suitable.

In a preferred process variant, the liquid distribution in the individual regions of the dividing wall column can be set separately in each case. Consequently, the total energy requirement for separating the mixture can be minimized.

In the regions of the feed section of the dividing wall column, with particular advantage, more liquid can be added in the wall region, and less liquid can be added in the wall region in regions of the dividing wall column. As a result, unwanted creep streams are avoided and the achievable final product purities are improved.

The dividing wall column can be equipped with stacked packings or dumped packings in one or more regions.

It is possible to design the dividing wall in the form of loosely inserted segments. This leads to a further cost reduction in the production and assembly of the dividing wall column.

Particularly advantageously, the loose dividing wall may have internal manholes or removable segments which make it possible to reach from one side of the dividing wall to the other side inside the dividing wall column.

Where the product purity has to meet particularly high requirements, it is advantageous to equip the dividing wall with thermal insulation, in particular where stacked packings are used as internals having a separating effect. Such a design of the dividing wall is described, for example, in EP-A-0 640 367. A double-wall version having a narrow gas space in between is particularly advantageous.

According to the invention, it is also possible to use thermally coupled columns instead of the dividing wall column. Arrangements comprising thermally coupled columns are equivalent to a dividing wall column in terms of the energy requirement. This variant of the invention is possible in particular where existing columns are available. The most suitable forms of interconnection can be chosen according to the number of theoretical plates of the columns present.

The thermally coupled columns can thus each be equipped with their own evaporator and/or condenser.

In a preferred process variant, only liquids are transported in the connecting streams between the two thermally coupled columns. This is particularly advantageous if the thermally coupled columns are operated at different pressures.

In a preferred interconnected arrangement of the thermally coupled columns, the low boiler fraction and the high boiler fraction are taken off from different columns, the operating pressure of the column from which the high boiler fraction is taken off being set from 0.1 to 2, in particular from 0.5 to 1, bar lower than the operating pressure of the column from which the low boiler fraction is taken off.

According to a particular form of interconnection, it is possible partly or completely to evaporate the bottom stream of the first column in an evaporator and then to feed it to the second column in two-phase form or in the form of a gaseous and a liquid stream.

With the use of a dividing wall column as well as of thermally coupled columns, the novel process can preferably be carried out in a manner such that the feed stream is partly or completely preevaporated and is fed to the column in two-phase form or in the form of a gaseous and a liquid stream.

This preevaporation is possible in particular when the bottom stream of the first column contains relatively large amounts of medium boilers. In this case, the preevaporation can be effected at a lower temperature level and the evaporator of the second column can be relieved. Furthermore, the stripping section of the second column is substantially relieved as a result of this measure. The preevaporated stream can be fed to the second column in two-phase form or in the form of two separate streams.

The dividing wall column for carrying out the novel process has, at the upper and at the lower end of the dividing wall, sampling facilities via which liquid and/or gaseous samples are taken continuously or at time intervals from the column and are investigated with regard to their composition, preferably by gas chromatography.

In the embodiment comprising thermally coupled columns, sampling facilities are arranged analogously in the connecting lines between those regions of the thermally coupled columns which correspond to the regions of the dividing wall column.

BRIEF DESCRIPTION OF THE DRAWINGS

The invention is explained in more detail below with reference to the following drawings and embodiments in which.

DETAILED DESCRIPTION

Figure 1:
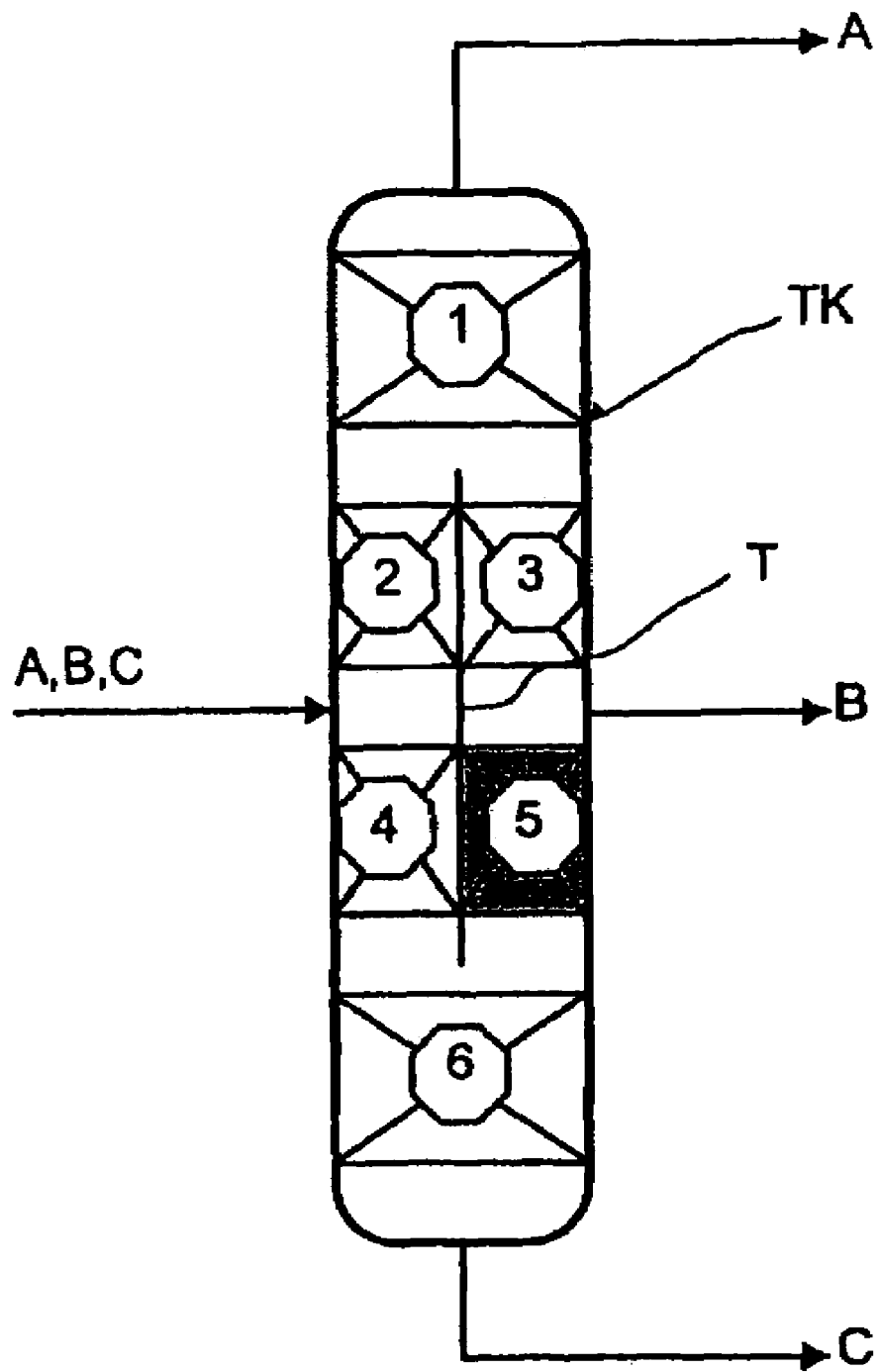
FIG. 1 shows a schematic diagram of a dividing wall column for carrying out the novel process; and, FIG. 2 shows schematic diagrams of thermally coupled columns for carrying out the novel process.
Figure 2:
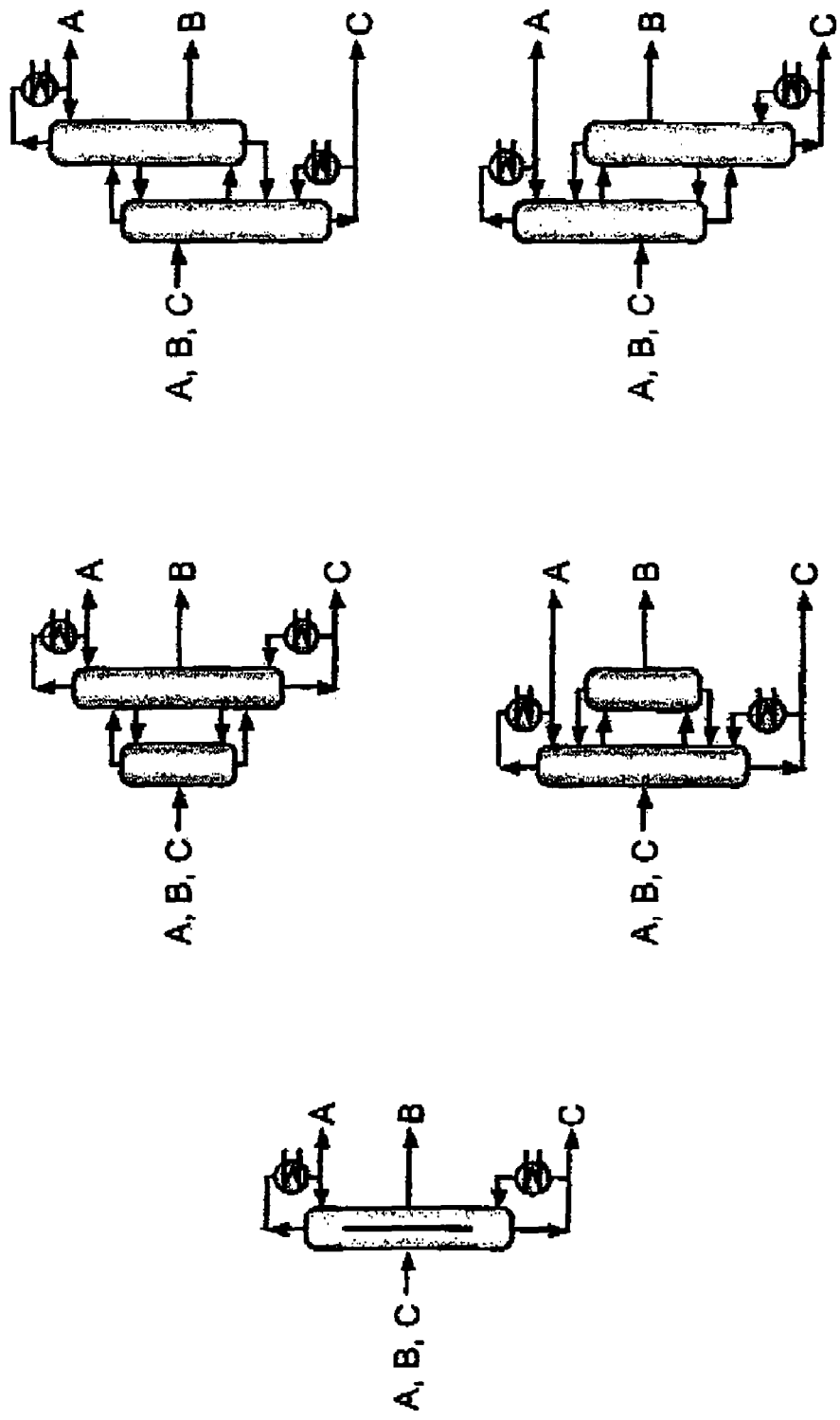

FIG. 1 schematically shows a dividing wall column (TK) having a dividing wall (T) which is arranged vertically therein and divides the column into an upper common column region 1, a lower common column region 6, a feed section 2, 4 having a rectification section 2 and stripping section 4, and a take-off section 3, 5 having a stripping section 3 and rectification section 5. The mixture (A, B, C) to be separated is fed in in the middle region of the feed section 2, 4. The low boiler fraction (A) is taken off at the top of the column, the high boiler fraction (C) from the bottom of the column and the medium boiler fraction (B) from the middle region of the take-off section 3, 5.

A novel dividing wall column was equipped with wire mesh packing and had 85 theoretical plates, comprising 18 theoretical plates in the lower common column region 6, 47 theoretical plates in the region of the dividing wall and 20 theoretical plates in the upper common column region 1. The dividing wall column was fed with a crude HDO stream which, in addition to HDO as the main component, contained about 20% by weight of low boilers, including predominantly PDO (about 10% by weight), 1,2-cyclohexanediol (about 4% by weight) and hexanol (about 0.2% by weight), and about 2.5% by weight of high boilers, including di-HDO ether as the main component, in an amount of 2% by weight. Moreover, a large number of further components, each in low concentration, were contained both in the low boiler fraction and in the high boiler fraction.

EXAMPLE 1

The dividing wall column was operated at a top pressure of 150 mbar and a reflux ratio of 20. The liquid at the upper end of the dividing wall was divided in equal parts between the feed section and the take-off section of the dividing wall column. The crude HDO stream was added to the 52nd theoretical plate, and the product, pure HDO, was taken off from the 28th theoretical plate. An on-spec product was obtained, i.e. a pure HDO containing 99% by weight of HDO.

EXAMPLE 2

The apparatus used for obtaining pure PDO from crude PDO by distillation was the same as that used for HDO (Example 1). However, the dividing wall column was operated at a top pressure of 100 mbar and a reflux ratio of 40. The liquid at the top of the dividing wall was divided in the ratio of about 44:56 between the feed section and the take-off section. The feed stream, the crude PDO, contained, in addition to PDO as the main component, 25% by weight of low boilers, including about 13% by weight of 1,2-cyclohexanediol, about 1.5% by weight of butanediol and about 2.6% by weight of valerolactone, and about 45% by weight of high boilers, including about 43% by weight of HDO as the main component.

The crude PDO was added to the 48th theoretical plate of the dividing wall column and the product, pure PDO, was taken off from the 40th theoretical plate. An on-spec pure PDO was obtained, i.e. a product containing at least 97% by weight of PDO.

EXAMPLE 3

A crude CLO which, in addition to CLO as the main component, contained about 2.5% by weight of low boilers, including predominantly methanol (0.9% by weight) and valerolactone (0.4% by weight), and about 0.5% by weight of high boilers, including predominantly dimeric caprolactone (about 0.05% by weight), formic acid/hydroxycaproic acid methyl ester (about 0.02% by weight) and hydroxycaproic acid methyl ester (about 0.02% by weight) was added to the same column as that described for Example 1. Moreover, a large number of components, each in low concentration, were contained in the low boiler fraction as well as in the high boiler fraction.

The dividing wall column was operated at a top pressure of 50 mbar and a reflux ratio of 38. The liquid at the upper end of the dividing wall was divided in the ratio of about 33:66 between the feed section and the take-off section. The crude PDO was added to the 32nd theoretical plate and the product, pure CLO, was taken off from the 32nd theoretical plate. An on-spec pure CLO was obtained, i.e. a product which contains at least 99% by weight of CLO.

We claim:

1. A process for working up by distillation crude products containing at least one of 1,6-hexanediol (HDO), 1,5-pentanediol (PDO) and caprolactone (CLO) to obtain corresponding purified products, wherein the working up by distillation is carried out in at least one of a dividing wall column (TK) and a thermally coupled column, wherein said dividing wall column consisting essentially of:
   a dividing wall arranged (T) in a longitudinal direction of the column;
   an upper common column region;
   a lower common column region;
   a feed section having a rectification section and stripping section; and,
   a take-off section having a stripping section and rectification section, wherein feeding of the respective crude products containing said at least one of HDO, PDO and CLO occurs in a middle region of the feed section and removal of a high boiler fraction (C) occurs at a bottom of the column, removal of a low boiler fraction (A) occurs at a top of the column, and removal of a medium boiler fraction (B) occurs at a middle region of the take-off section.

2. A process as claimed in claim 1, wherein the medium boiler fraction (B) is taken off in liquid form.

3. A process as claimed in claim 1, wherein a vapor stream at the lower end of the dividing wall (T) is set in a manner such that a ratio of a vapor stream in the feed section to the vapor stream in the take-off section is from 0.8 to 1.2.

4. A process as claimed in claim 3, wherein the ratio is from 0.9 to 1.1.

5. A process as claimed in claim 1, wherein a reflux stream from the upper common column section is regulated so that a ratio of the reflux stream in the feed section to a reflux in the take-off section is from 0.1 to 1.0.

6. A process as claimed in claim 5, wherein the ratio is from 0.5 to 0.8.

7. A process as claimed in claim 1, wherein liquid distribution in individual regions 1 to 6 of the dividing wall column (TK) can be set separately in each case.

8. A process as claimed in claim 1 wherein said dividing wall column (TK) comprises from 30 to 100 theoretical plates.

9. A process as claimed in claim 8 wherein said dividing wall comprises from 50 to 90 plates.

10. A process as claimed in claim 8, wherein sampling facilities are set up at the upper and the lower end of the dividing wall (TK), via which facilities liquid and/or gaseous samples are taken continuously or at time intervals from the column and are investigated with regard to their composition.

11. A process as claimed in claim 10, wherein the investigation is conducted by gas chromatography.

12. A process as claimed in claim 8, wherein the feed point of a stream (A, B, C) and the take-off point of the medium boiler stream (B) are arranged at different heights in the column theoretical plates apart.

13. A process as claimed in claim 12, wherein the points are arranged from 1 to 20 plates.

14. A process as claimed in claim 12, wherein the points are arranged from 10 to 15 points.

15. A process as claimed in claim 8, wherein at least one of regions 2, 3, 4 and 5 of the dividing wall column (TK) is equipped with at least one of stacked packings and dumped packings and the dividing wall (T) is made heat-insulating in areas adjoining one or more of the regions 2, 3, 4 and 5.

16. A process as claimed in claim 8, wherein the dividing wall (T) is in the form of loosely inserted segments.

17. A process as claimed in claim 16, wherein the loose dividing wall (T) has at least one of internal manholes or removable segments to reach from one side of the dividing wall (T) to an other side inside the dividing wall column (TK).

18. A process as claimed in claim 1 using thermally coupled columns, wherein two thermally coupled columns are operated at different pressures and/or wherein only liquids are transported in connecting streams between the two thermally coupled columns.

19. A process as claimed in claim 18, wherein a low boiler fraction (A) and a high boiler fraction (C) are taken off from different columns, and an operating pressure of the column from which the high boiler fraction (C) is taken off is set bar lower than an operating pressure of the column from which the low boiler fraction (A) is taken off.

20. A process as claimed in claim 19, wherein the pressure is from 0.1 to 2 bar.

21. A process as claimed in claim 20, wherein the pressure is from 0.5 to 1 bar.

22. A process as claimed in claim 18 wherein each said thermally coupled columns have at least one of an evaporator and condenser.

23. A process as claimed in claim 1 using thermally coupled columns, wherein a bottom stream of a first column is partially or completely evaporated in an evaporator and is then fed to a second column in two-phase form or in the form of a gaseous and a liquid stream.

24. A process for working up by distillation crude products containing at least one of 1,6-hexanediol (HDO), 1,5-pentanediol (PDO) and caprolactone(CLO) to obtain corresponding purified products, wherein the working up by distillation is carried out in at least one of a dividing wall column (TK) and a thermally coupled column, said dividing wall column comprising:
 a dividing wall arranged (T) in a longitudinal direction of the column;
 an upper common column region;
 a lower common column region;
 a feed section having a rectification section and stripping section; and,
 a take-off section having a stripping section and rectification section, wherein feeding of the respective crude products containing said at least one of HDO, PDO and CLO occurs in a middle region of the feed section and removal of a high boiler fraction occurs at a bottom of the column, removal of a low boiler fraction (A) occurs at a top of the column and removal of a medium boiler fraction (B) occurs at a middle region of the take-off section, wherein a distribution ratio of a liquid reflux at an upper end of the dividing wall (T) is set such that a proportion of high-boiling key components in the liquid reflux via the stripping section of the take-off section at the upper end of the dividing wall (T) is from 10 to 80% of a limit permitted in the medium boiler fraction (B), and wherein a heating power in a bottom evaporator of the dividing wall column (TK) is set such that a concentration of low-boiling key components in the liquid at a lower end of the dividing wall (T) is from 10 to 80% of the limit permitted in the medium boiler fraction (B).

25. A process as claimed in claim 24, wherein the proportion is from 30 to 50% and the concentration is from 30 to 50%.

26. A process for working up by distillation crude products containing at least one of 1,6-hexanediol (HDO), 1,5-pentanediol (PDO) and caprolactone (CLO) to obtain corresponding purified products, wherein the working up by distillation is carried out in at least one of a dividing wall column (TK) and a thermally coupled column, wherein said dividing wall column comprises:
 a dividing wall arranged (T) in a longitudinal direction of the column;
 an upper common column region;
 a lower common column region;
 a feed section having a rectification section and stripping section; and,
 a take-off section having a stripping section and rectification section, wherein feeding of the respective crude products containing said at least one of HDO, PDO and CLO occurs in a middle region of the feed section and removal of a high boiler fraction (C) occurs at a bottom of the column, removal of a low boiler fraction (A) occurs at a top of the column, and removal of a medium boiler fraction (B) occurs at a middle region of the take-off section, wherein a HDO purification column and a PDO purification column are connected in a manner such that HDO fractions remaining in a top stream of the HDO purification column are recovered via the bottom of the PDO purification column and are recycled to the HDO purification column.

27. A process as claimed in claim 26, wherein column regions 1 to 6 each have from 5 to 50% of the total number of theoretical plates of the dividing wall column (TK).

28. A process as claimed in claim 27, wherein the regions have from 15 to 30% of the number.

29. A process for working up by distillation crude products containing at least one of 1,6-hexanediol (HDO), 1,5-pentanediol (PDO) and caprolactone (CLO) to obtain corresponding purified products, wherein the working up by distillation is carried out in at least one of a dividing wall column (TK) and a thermally coupled column, wherein said dividing wall column comprises:
 a dividing wall arranged (T) in a longitudinal direction of the column;
 an upper common column region;
 a lower common column region;
 a feed section having a rectification section and stripping section; and,
 a take-off section having a stripping section and rectification section, wherein feeding of the respective crude products containing said at least one of HDO, PDO and CLO occurs in a middle region of the feed section and removal of a high boiler fraction (C) occurs at a bottom of the column, removal of a low boiler fraction (A) occurs at a top of the column, and removal of a medium boiler fraction (B) occurs at a middle region of the take-off section, wherein a flow rate of the crude product fed to the middle region of the feed section is regulated in a manner such that it does not fall below 30% of its normal value.

30. A process for working up by distillation crude products containing at least one of 1,6-hexanediol (HDO), 1,5-pentanediol (PDO) and caprolactone (CLO) to obtain corresponding purified products, wherein the working up by distillation is carried out in at least one of a dividing wall column (TK) and a thermally coupled column, wherein said dividing wall column comprises:
 a dividing wall arranged (T) in a longitudinal direction of the column;
 an upper common column region;
 a feed section having a rectification and stripping section; and,
 a take-off section having a stripping section and rectification section, wherein feeding of the respective crude products containing said at least one of HDO, PDO and CLO occurs in a middle region of the feed section and removal of a high boiler fraction (C) occurs at a bottom of the column, removal of a low boiler fraction (A) occurs at a top of the column, and removal of a medium boiler fraction (B) occurs at a middle region of the take-off section, wherein distribution of a liquid flowing out of the stripping section of the take-off section of the dividing wall column (TK) between the medium boiler fraction (B) taken off and the rectification section of the take-off section of the dividing wall column (TK) is established by regulation in a manner such that an amount of liquid added to the rectification section does not fall below 30% of its normal value.

31. A process for working up by distillation crude products containing at least one of 1,6-hexanediol (HDO), 1,5-pentanediol (PDO) and caprolactone (CLO) to obtain corresponding purified products, wherein the working up by distillation is carried out in at least one of a dividing wall column (TK) and a thermally coupled column, wherein said dividing wall column comprises:
 a dividing wall arranged (T) in a longitudinal direction of the column;
 an upper common column region;
 a lower common column region;
 a feed section having a rectification section and stripping section; and,
 a take-off section having a stripping section and rectification section, wherein feeding of the respective crude products containing said at least one of HDO, PDO and CLO occurs in a middle region of the feed section and removal of a high boiler fraction (C) occurs at a bottom of the column, removal of a low boiler fraction (A) occurs at a top of the column, and removal of a medium boiler fraction (B) occurs at a middle region of the take-off section, wherein the low boiler fraction (A) is taken off in a temperature-controlled manner, a measuring point for the control temperature in the upper common region of the column being arranged at a point which is from 3 to 8 theoretical plates below the upper end of the column.

32. The process as recited in claim 31 wherein removal of a medium boiler fraction (B) occurs at a middle region of the take-off section, wherein the low boiler fraction (A) is taken off in a temperature-controlled manner, a measuring point for the control temperature in the upper common region of the column being arranged at a point which is from 3 to 8 theoretical plates below the upper end of the column, and wherein the point is from 4 to 6 theoretical plates.

33. A process for working up by distillation crude products containing at least one of 1,6-hexanediol (HDO), 1,5-pentanediol (PDO) and caprolactone (CLO) to obtain corresponding purified products, wherein the working up by distillation is carried out in at least one of a dividing wall column (TK) and a thermally coupled column, wherein said dividing wall column comprises:
   a dividing wall arranged (T) in a longitudinal direction of the column;
   an upper common column region;
   a lower common column region;
   a feed section having a rectification section and stripping section; and,
   a take-off section having a stripping section and rectification section, wherein feeding of the respective crude products containing said at least one of HDO, PDO and CLO occurs in a middle region of the feed section and removal of a high boiler fraction (C) occurs at a bottom of the column, removal of a low boiler fraction (A) occurs at a top of the column, and removal of a medium boiler fraction (B) occurs at a middle region of the take-off section wherein the high boiler fraction (C) is taken off in a temperature-controlled manner, a measuring point for the control temperature in the lower common region of the column being arranged at a point which is from 3 to 8 theoretical plates above the lower end of the column.

34. The process as recited in claim 33 wherein the high boiler fraction (C) is taken off in a temperature-controlled manner, a measuring point for the control temperature in the lower common column region being arranged from 3 to 8 theoretical plates above the lower end of the column.

35. The process as recited in claim 34 wherein the measuring point is from 4 to 6 theoretical plates.

36. A process for working up by distillation crude products containing at least one of 1,6-hexanediol (HDO), 1,5-pentanediol (PDO) and caprolactone (CLO) to obtain corresponding purified products, wherein the working up by distillation is carried out in at least one of a dividing wall column (TK) and a thermally coupled column, wherein said dividing wall column comprises:
   a dividing wall arranged (T) in a longitudinal direction of the column;
   an upper common column region;
   a lower common column region;
   a feed section having a rectification section and stripping section; and,
   a take-off section having a stripping section and rectification section, wherein feeding of the respective crude products containing said at least one of HDO, PDO and CLO occurs in a middle region of the feed section and removal of a high boiler fraction (C) occurs at a bottom of the column, removal of a low boiler fraction (A) occurs at a top of the column, and removal of a medium boiler fraction (B) occurs at a middle region of the take-off section, wherein the medium boiler fraction (B) is taken off under level control, and a liquid level in an evaporator or in the bottom of the column is used as a control variable.

37. A process for working up by distillation crude products containing at least one of 1,6-hexanediol (HDO), 1,5-pentanediol (PDO) and caprolactone (CLO) to obtain corresponding purified products, wherein the working up by distillation is carried out in at least one of a dividing wall column (TK) and a thermally coupled column, wherein said dividing wall column comprises:
   a dividing wall arranged (T) in a longitudinal direction of the column;
   an upper common column region;
   a lower common column region;
   a feed section having a rectification section and stripping section; and,
   a take-off section having a stripping section and rectification section, wherein feeding of the respective crude products containing said at least one of HDO, PDO and CLO occurs in a middle region of the feed section and removal of a high boiler fraction (C) occurs at a bottom of the column, removal of a low boiler fraction (A) occurs at a top of the column, and removal of a medium boiler fraction (B) occurs at a middle region of the take-off section, wherein more liquid is added in a wall region in regions 2 to 4 of the dividing wall column (TK) and less liquid is added in a wall region in regions 3 and 5 of the dividing wall column (TK).

* * * * *

UNITED STATES PATENT AND TRADEMARK OFFICE
CERTIFICATE OF CORRECTION

| | |
|---|---|
| PATENT NO. | : 7,329,330 B2 |
| APPLICATION NO. | : 10/451738 |
| DATED | : February 12, 2008 |
| INVENTOR(S) | : Gall et al. |

It is certified that error appears in the above-identified patent and that said Letters Patent is hereby corrected as shown below:

Claim 24, column 9, line 14: "high boiler fraction occurs" should read --high boiler fraction (C) occurs--

Signed and Sealed this

Twenty-fourth Day of June, 2008

JON W. DUDAS
*Director of the United States Patent and Trademark Office*